United States Patent
Kido et al.

(10) Patent No.: US 9,999,594 B2
(45) Date of Patent: *Jun. 19, 2018

(54) THERAPEUTIC OR PREVENTIVE AGENT FOR MEIBOMIAN GLAND DYSFUNCTION OR MEIBOMIAN GLAND BLOCKAGE

(71) Applicant: Santen Pharmaceutical Co., Ltd., Osaka-shi, Osaka (JP)

(72) Inventors: Kazutaka Kido, Ikoma (JP); Takashi Nagano, Ikoma (JP)

(73) Assignee: SANTEN PHARMACEUTICAL CO., LTD., Osaka (JP)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/363,583

(22) Filed: Nov. 29, 2016

(65) Prior Publication Data

US 2017/0071852 A1    Mar. 16, 2017

Related U.S. Application Data

(63) Continuation of application No. 14/670,999, filed as application No. PCT/JP2012/075119 on Sep. 28, 2012, now Pat. No. 9,539,204.

(51) Int. Cl.
| | | |
|---|---|---|
| A61K 31/7048 | (2006.01) | |
| A61K 9/00 | (2006.01) | |
| A61K 47/06 | (2006.01) | |
| A61K 47/14 | (2017.01) | |
| A61K 9/06 | (2006.01) | |
| A61K 9/08 | (2006.01) | |
| A61K 9/10 | (2006.01) | |
| A61K 47/38 | (2006.01) | |

(52) U.S. Cl.
CPC ........... *A61K 9/0048* (2013.01); *A61K 9/06* (2013.01); *A61K 9/08* (2013.01); *A61K 9/10* (2013.01); *A61K 31/7048* (2013.01); *A61K 47/06* (2013.01); *A61K 47/14* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 5,629,297 A | 5/1997 | McColm | |
| 7,811,599 B2 | 10/2010 | Lukacs et al. | |
| 9,539,204 B2 * | 1/2017 | Kido .................. | A61K 47/06 |
| 2005/0043222 A1 | 2/2005 | Lukacs et al. | |
| 2011/0206620 A1 | 8/2011 | Dana et al. | |

FOREIGN PATENT DOCUMENTS

| | | |
|---|---|---|
| CN | 1452977 A | 11/2003 |
| CN | 1475220 A | 2/2004 |
| CN | 1850045 A | 10/2006 |
| JP | H0692850 A | 4/1994 |
| JP | H11147827 A | 6/1999 |
| JP | 2006241172 A | 9/2006 |
| RU | 2291694 C2 | 1/2007 |
| WO | 2011106697 A1 | 9/2011 |

OTHER PUBLICATIONS

Kinoshita et al., Cornea, 2009, vol. 28, pp. S3-S6.*
Yokoi et al., Japanese Review of Clinical Ophthalmology, vol. 99, No. 8, 2005, 2 pages.*
Otiz et al., Ophthalmology, 2011, vol. 82, pp. 92-103.*
Gross et al., Investigative Ophthalmology and Visual Science, Apr. 1995, vol. 36, No. 5, pp. 965-968.*
Abstract of: Finis D. et al. Meibomian gland dysfunction. Klin. Monbl.Augenheilkd. May 2012; 229(5):506-13.
Amano, Shiro, "Meibom-sen Kino Fuzen no Kangaekata 1. Teigi/Shindan Kijun to MGD no Saikin no Kangaekata", Ophthalmology, 2010, vol. 52, No. 12, pp. 1751-1756.
Asbell, P.A. et al, The International Workshop on Meibomian Gland Dysfunction: Report of the Clinical Trials Subcommittee, IOVS, 2011, vol. 52, No. 4, p. 2065-2085.
Bergfeld,W.F., A lifetime of healthy skin: implications for women, Int J Fertil Womens Med, 1999, vol. 44, No. 2, pp. 83-95.
Chinese Office Action issued to Application No. 201280074718.4; dated Jul. 14, 2015.
Efficacy of azithromycin 1% ophthalmic solution for treatment of ocular surface disease from posterior blepharitis. Clinical and Experimental Optometry. 2011. vol. 94, No. 2, pp. 200-206.
Extended European search report for European Patent Application No. 12885416.3-1466/2902023 PCT/JP2012/075119; dated Mar. 2, 2016.
Foulks, G.N. et al, Meibomian gland dysfunction: a clinical scheme for description, diagnosis, classification, and grading, Ocul Surf, 2003, vol. 1, No. 3, p. 107-26.
Goto, E. et al, Low-concentration homogenized castor oil eye drops for noninflamed obstructive meibomian gland dysfunction, Ophthalmology, 2002, vol. 109, No. 11, p. 2030-5.
Goto, Hideki, Yamashita, Akiko, "Q&A20 Me no Kayumi no Genin ni Meibom-senen mo Aru to Kikimashita ga Honto Desu ka?", Q&A de Wakaru Allergy Shikkan, 2009, vol. 5, No. 1, pp. 884-886.
Hatano, H. et al, TE-031 (A-56268) in ophthalmology, Chemotherapy, 1988, vol. 36, NoSUPPL, p. 1101-1108, entire text.
Hiroshi Hatano, Kazuyo Wakamatsu: "TE-031 (A-56268) in ophthalmology", Chemotherapy, vol. 36, No. Suppl. 3 Jan. 1, 1988 (Jan. 1, 1988), pp. 1109-1113, XP002754380.
International Preliminary Report on Patenability corresponding to Application No. PCT/JP2012/075119; dated Sep. 25, 2015.
Kinoshita,S.D., Paradigm shift in therapeutic modalities for devastating ocular surface disorders, Cornea, 2009, vol. 28, No. SUPPL, p. S3-S6, entire text.

(Continued)

*Primary Examiner* — Traviss C McIntosh, III
(74) *Attorney, Agent, or Firm* — Cantor Colburn LLP

(57) ABSTRACT

The objective of the present invention is to provide a new medicinal use of clarithromycin. The present invention is a therapeutic agent or a preventive agent for meibomian gland dysfunction or meibomian gland blockage and comprises clarithromycin as an active ingredient. The dosage form is preferably an eye drop or eye ointment.

8 Claims, No Drawings

(56) References Cited

OTHER PUBLICATIONS

Korb, D.R. et al, Meibomian gland dysfunction and contact lens intolerance, J Am Optom Assoc, 1980, vol. 51, No. 3, p. 243-51.
Korean Office Action corresponding to Application No. 10-2015-7003637; dated Aug. 7, 2015.
Long term Oral Low Dose Clarithromycin Treatment for Meibomitis Associated Corneal Disorder. The Ocular Surface. 2005. vol. 3, No. 1, S124.
Makiko Takagi et al., "Meibom-sen'en Kakumaku Johisho no Chiryo", Japanese review of Clinical ophthalmology, 2005, vol. 99, No. 6, p. 514, entire text.
Mathers W, Dry Eye and Ocular Surface Disorders, Marcel Dekker, Inc. 2004, p. 247-267.
Nelson, J.D. et al, The international workshop on meibomian gland dysfunction: report of the definition and classification subcommittee, Invest Ophthalmol Vis Sci, 2011, vol. 52, No. 4, p. 1930-7.
Norihiko Yokoi et al., "Meibom-sen'en Kakumaku Johisho ni Taisuru Macrolide Shoryo Choki Ryoho", Japanese review of Clinical ophthalmology, 2005, vol. 99, No. 8, p. 682, entire text.
Norihiko Yokoi, "Meibom-sen ni Kanrenshita Gan Hyomen Shikkan", Japan Medical Journal, 2004, No. 4166, pp. 33 to 36, entire text.
Obata, H., Anatomy and histopathology of human meibomian gland, Cornea 2002, vol. 21, No. 7 Suppl, p. S70-4.
Ooishi M.; Sakaue F.; Oomomo A.; Tazawa h.: "TE-031 (A-56268) in the treatment of ocular infections", Chemotherapy, vol. 36, No. Suppl. 3 Jan. 1, 1988 (Jan. 1, 1988), pp. 1101-1108, XP002754378.
Rolando M, Diagnosis and management of the lid and ocular surface disorders, The Clinician's Guide to Diagnosis and Treatment, 2006, p. 63-83.
Russian Office Action corresponding to Application No. 2015108281; dated Sep. 18, 2015, with English translation.
Shimazaki, Jun, "Meibom-sen no Subete: Meibom-sen Kino Fuzen to Dry Eye", Journal of the Eye, 2001, vol. 18, No. 3, pp. 311-315.
Shiro Amano et al., "Definition and Diagnostic Criteria for Meibomian Gland Dysfunction", Journal of the Eye, 2010, vol. 27, No. 5, pp. 627 to 631, entire text.
The International Workshop on Meibomian Gland Dysfunction: Report of the Subcommittee on Management and Treatment of Meibomian Gland Dysfunction. Investigative Ophthalmology & Visual Science. 2011. vol. 52, No. 4, pp. 2050-2064.
Tomo Suzuki, "Gan Kansensho no Nazo o Toku II. Gan Kansensho Jiten 1. Ganken'en 3) Meibom-sen'en to Kanren Kakumaku Johi Shogai", Practical Ophthalmology, 2009, vol. 28, pp. 72 to 73, entire text.
U.S. Non Final Office Action corresponding to U.S. Appl. No. 14/670,999 dated Jan. 22, 2016.
Oltz et al., "Rosacea and its ocular manifestations", Ophthalmology, 2011, vol. 82, pp. 92-103.
Uchino et al., "Tear Film & Ocular Surface", The Ocular Surface, Jan. 2005, vol. 3, No. 1, Supplement p. S124.

* cited by examiner

THERAPEUTIC OR PREVENTIVE AGENT FOR MEIBOMIAN GLAND DYSFUNCTION OR MEIBOMIAN GLAND BLOCKAGE

CROSS REFERENCE TO RELATED APPLICATIONS

The present application is a continuation application of U.S. patent application Ser. No. 14/670,999, filed on Mar. 27, 2015, the entire contents of which are incorporated herein by reference and priority to which is hereby claimed. application Ser. No. 14/670,999 is the U.S. National stage of application No. PCT/JP2012/075119, filed on Sep. 28, 2012, the disclosure of which is also incorporated herein by reference.

TECHNICAL FIELD

The present invention relates to a therapeutic or preventive agent for meibomian gland dysfunction or meibomian gland concretion.

BACKGROUND ART

There are approximately 25 meibomian glands in the upper eyelid and approximately 20 meibomian glands in the lower eyelid of the human eye, and lipids are secreted from the meibomian gland orifices. Meibomian gland dysfunction (MGD) is a condition where a diffuse abnormality of the function of the meibomian glands is induced by various causes, and is accompanied by chronic ocular discomfort. Further, meibomian gland concretion is a condition where meibomian glands are obstructed by a white non-opaque oily clot formed in the duct because of decreased meibomian gland function.

On the other hand, clarithromycin is a macrolide antibiotic, which has been used for therapy of pharyngitis, tonsillitis, pneumonia, skin infections, acute exacerbation of chronic bronchitis and the like based on its antibacterial effect. Recently, aside from antibacterial effects, clarithromycin has been found to have antiinflammatory, immunoregulatory, and antibacterial biofilm effects, and based on these novel effects, starting with the therapy of endometriosis or fibroids, gastrointestinal disorders, and pruritus, the use of clarithromycin has also been proposed for acute exacerbation of chronic bronchitis, bronchial asthma, influenza virus infection, atopic dermatitis, rheumatoid arthritis, etc. (Patent Publications 1, 2, and 3).

Patent Document 1: Japanese Unexamined Patent Application, Publication No. 2006-241172
Patent Document 2: Japanese Unexamined Patent Application, Publication No. H06-92850
Patent Document 3: Japanese Unexamined Patent Application, Publication No. H11-147827

DISCLOSURE OF THE INVENTION

Problems to be Solved by the Invention

Thus, the investigation of novel medical applications of clarithromycin is a subject of great interest.

Means for Solving the Problems

The present inventors sought and diligently researched novel medical applications of clarithromycin, and discovered that (1) in tests of meibomian gland peripheral telangiectasia due to the administration of complete Freund's adjuvant using rats, clarithromycin notably improved the telangiectasia score, and (2) in tests of obstruction meibomian gland orifices due to feeding an HR-AD diet using hairless mice, clarithromycin notably reduced the number of obstructions of the meibomian gland orifices, and improved the obstructions, and thus completed the present invention.

Namely, the present invention is therapeutic agent or preventive agent for meibomian gland dysfunction or meibomian gland concretion comprising clarithromycin as the effective component.

Effects of the Invention

Thus, it is expected that a formulation comprising clarithromycin as the effective component will be effective for therapy or prevention of meibomian gland dysfunction or meibomian gland concretion.

PREFERRED MODE FOR CARRYING OUT THE INVENTION

Below, embodiments of the present invention are explained.

The clarithromycin of the present invention can be easily produced by a conventional method, or obtained commercially.

Meibomian gland dysfunction (MGD) is a condition where diffuse abnormality of the meibomian glands is induced by various causes, and is accompanied with chronic ocular discomfort. Meibomian gland dysfunction can be categorized by a condition of the secretion of the meibomian glands, and can be divided into reduced secretion type and increased secretion type, and in clinical practice, the reduced secretion type is more common than the increased secretion type.

Reduced secretion type meibomian gland dysfunction is a condition where the secretion of the meibomian lipid is reduced by the accumulation of excess keratinized substances in the duct of the meibomian gland, or by the obstruction of the meibomian gland orifices by various causes. Finding of obstructions of the meibomian gland orifices or finding of abnormalities surrounding the meibomian gland orifices (telangiectasia, displacement of the mucocutaneous junction, irregularity of the eyelid margins, and the like) are considered to be pathognomic findings of reduced secretion type meibomian gland dysfunction.

Increased secretion type meibomian gland dysfunction is a disorder where lipid secretion of the meibomian glands is excessive, and has the characteristic that large quantities of meibomian gland lipids are discharged to the eyelid margins in reaction to compression of the tarsus.

Meibomian gland concretion is a condition where a mixture of keratinized substances and lipids is concreted in the duct of the meibomian gland, and obstruction of the orifice of the meibomian gland is considered as a characteristic finding.

As induced symptoms accompanying meibomian gland dysfunction or meibomian gland concretion, there are many symptoms such as ocular discomfort, burning sensations, itching and the like.

The therapeutic agent or preventive agent for meibomian gland dysfunction or meibomian gland concretion of the present invention can be administered orally or parenterally. As the dosage form, dosage forms for parenteral use such as ophthalmic solutions, ophthalmic ointments, injections and the like, and dosage forms for oral administration such as tablets, capsules, granules, powders and the like may be mentioned, and in particular, ophthalmic solutions are particularly preferable.

The formulation thereof can be carried out using generally used techniques. For example, in the case of an ophthalmic solution, a tonicity agent such as sodium chloride or concentrated glycerin and the like; a buffer such as sodium phosphate, sodium acetate and the like; a surfactant such as polyoxyethylene sorbitan monooleate, polyoxyl 40 stearate, polysorbate 80, polyoxyethylene hydrogenated castor oil and the like; a stabilizer such as sodium citrate or sodium edetate and the like; and a preservative such as benzalkonium chloride, paraben and the like; and the like may be used as needed. The pH may be within the allowable range of ophthalmic solutions, and is preferably in the range of 4 to 8.

In the case of an ophthalmic ointment, the formulation may be carried out using a general purpose base such as white petrolatum, liquid paraffin, and the like.

In the case of oral preparations such as tablets, capsules, granules, powders and the like, the formulation may be carried out using an extender such as lactose, crystalline cellulose, starch, vegetable oil and the like; a lubricant such as magnesium stearate, talc and the like; a binder such as hydroxypropyl cellulose, polyvinyl pyrrolidone and the like, a disintegrant such as carboxylmethyl cellulose calcium, low-substituted hydroxypropylmethyl cellulose and the like, a coating agent such as hydroxypropylmethyl cellulose, macrogol, a silicon resin and the like; a film forming agent such as gelatin film and the like; and the like, as needed.

The dose of clarithromycin can be properly selected depending on the symptoms, age, dosage form and the like, and in the case of an ophthalmic solution, a formulation of from 0.0001 to 5% (w/v), preferably from 0.01 to 3% (w/v), may be dropped into the eye on the order of from 1 to 6 times/day. In the case of an oral preparation, clarithromycin may be usually administered at from 0.1 to 5000 mg per day, preferably 1 to 1000 mg per day, at once or divided into several doses.

The present invention includes the following inventions.

(1) Clarithromycin for use in the therapy or prevention of MGD or meibomian gland concretion.

(2) Clarithromycin as recited above in item (1) formulated as a dosage form of an ophthalmic solution or an ophthalmic ointment.

(3) Use of clarithromycin for manufacturing a medicament for therapy or prevention of MGD or meibomian gland concretion.

(4) The use as recited above in item (3) wherein the dosage form of the medicament is an ophthalmic solution or an ophthalmic ointment.

EXAMPLES

Hereinafter, preparation examples and results of pharmacological tests are shown, but these examples are to facilitate understanding of the present invention and do not limit the scope of the present invention.

Preparation Example 1

In 100 ml,
Clarithromycin 1 g
Concentrated glycerin 2 g
Dibasic sodium phosphate hydrate 0.1 g
Polyoxyl 40 stearate 0.1 g
Diluted hydrochloric acid/sodium hydroxide q.s.
Sterile purified water q.s.
pH 7.0

By altering the amount of clarithromycin to be added, solution-type ophthalmic solutions at concentrations of 0.01% (w/v), 0.1% (w/v) or 1.0% (w/v) could be prepared.

Preparation Example 2

In 100 ml,
Clarithromycin 1 g
Sodium chloride 0.75 g
Disodium hydrogen phosphate 0.06 g
Sodium dihydrogen phosphate 0.6 g
Polysorbate 80 0.005 g
Hydroxypropyl methyl cellulose 0.001 g
Sodium edetate hydrate 0.01 g
Diluted hydrochloric acid/sodium hydroxide q.s.
Sterile purified water q.s.
pH 7.0

By altering the amount of clarithromycin to be added, suspension-type ophthalmic solutions at concentrations of 0.1% (w/v) or 0.5% (w/v) could be prepared.

Preparation Example 3

In 100 ml,
Clarithromycin 2 g
Liquid paraffin 30 g
White soft paraffin q.s.

By altering the amount of clarithromycin to be added, ophthalmic ointments at concentrations of 1% (w/w) or 5% (w/w) could be prepared.

Pharmacological Tests

1. Test for Meibomian Gland Peripheral Telangiectasia by Administration of Full Friend's Adjuvant Using Rats (Method for Preparation of Test Sample)

Clarithromycin (LKT Laboratories, Inc.), concentrated glycerin, dibasic sodium phosphate hydrate and polyoxyl 40 stearate were added to purified water and dissolved to prepare a test sample comprising clarithromycin at a final concentration of 1% (w/v), at pH 7.

(Test Method)

Twenty five µl of complete Freund's adjuvant was administered to one site of the right upper eyelid of female Lewis rats at five weeks age. On the seventh day from the initiation, the periphery of the meibomian gland orifices on the right upper eyelid was observed using a slit-lamp and a telangiectasia score was determined. The eyelid margin of the upper eyelid was divided into three segments: ear, middle and nasal sites, and based on criteria described in Table 1, scores of telangiectasia peripheral to the meibomian gland orifices in each segment were determined and the sum of the scores in three segments were calculated as the telangiectasia score of one eye. The presence or absence of dilation of the capillaries was determined based on whether a capillary that is usually not visible could be ascertained as a result of enlargement of the capillary diameter.

TABLE 1

| Score | Condition of telangiectasia in the vicinity of meibomian gland orifices |
|---|---|
| 0 | Dilation of the capillaries is not recognized at the periphery of the meibomian gland orifices when eyelid is in opened state. |

TABLE 1-continued

Condition of telangiectasia in the vicinity of meibomian gland
Score orifices

1  Dilation of a few capillaries is recognized at the periphery
   of the meibomian gland orifices when eyelid is in opened state.
2  Moderate dilation of the capillaries or slight redness is visible
   at the periphery of the meibomian gland orifices when eyelid is in
   opened state.
3  Redness and severe telangiectasia are visible surrounding
   meibomian gland orifices when eyelid is in opened state.

After dividing into a saline-administered group and a 1% (w/v) clarithromycin aqueous solution-administered groups, the test was carried out with six eyes in each group so as to minimize variations in mean scores, and from the 8th day after initiation, saline (5 μl/eye, six times per day) or 1% (w/v) clarithromycin aqueous solution (5 μl/eye, three or six times per day) were instilled into the right eyes for 21 days. At 28 days after initiation, the peripheries of the meibomian gland orifices on the right upper eyelids were observed using a slit-lamp and the telangiectasia score was determined.
(Results)
The results (the means of the telangiectasia scores) are shown in Table 2.

TABLE 2

|  | Telangiectasia score | |
|---|---|---|
|  | 7 days after initiation (day 0 from start of administration) | 28 days after initiation (day 21 from start of administration) |
| Saline-administered group | 5.3 | 4.3 |
| 1% clarithromycin aqueous solution-administered group (instilled 3 times per day) | 5.3 | 2.8 |
| 1% clarithromycin aqueous solution-administered group (instilled 6 times per day) | 5.3 | 2.5 |

(Discussion)
At seven days from the initiation (day 0 from the start of administration), no difference was recognized in the means of the telangiectasia scores of each group, but 28 days after initiation (day 21 from the start of administration), the telangiectasia score in the vicinity of the meibomian gland orifices in the 1% clarithromycin aqueous solution-administered group (instilled three or six times per day) was remarkably lower compared to the saline-administered group.

2. Test for Obstruction of Meibomian Gland Orifices by Feeding HR-AD Diet Using Hairless Mice
(Method for Preparation of Test Sample)
A 1% (w/v) clarithromycin test solution was prepared by the same operation as described in Pharmacological Test 1.
(Test Method)
Male Hos:HR-1 hairless mice at five weeks of age were divided into a group of 6 fed a regular diet (CRF-1 diet, manufactured by Oriental Yeast Co., Ltd.); and a group of 12 fed an HR-AD diet (manufactured by Nosan Corporation), and the mice in each respective group were freely allowed to feed the regular diet or HR-AD diet. On the 28th day after the start of the diets, meibomian gland orifices were observed using a slit-lamp and the number of obstructed orifices out of eight meibomian gland orifices of the center of the right upper eyelid were counted. The presence or absence of an obstruction of the meibomian gland orifice was determined based on whether the meibomian gland orifice was in a cloudy and swollen state.

The 12 mice in the HR-AD diet group were further divided into a saline-administered group; and a 1% (w/v) clarithromycin aqueous solution-administered group, and testing was carried out with six eyes in each group so as to minimize variations in the mean scores of the number of obstructed meibomian gland orifices in each group; from the 29th day after starting the diets, saline (2 μl/eye, three times per day) or 1% (w/v) clarithromycin aqueous solution (2 μl/eye, three times per day) were instilled for 14 days. At 42 days after starting the diet, meibomian gland orifices were observed using a slit-lamp and the number of obstructed orifices out of eight meibomian gland orifices of the center of the right upper eyelid were counted.
(Results)
The results (the means of the number of obstructed orifice scores) are shown in Table 3.

TABLE 3

|  | Number of obstructed meibomian gland orifices | |
|---|---|---|
|  | 28 days after starting feeding (day 0 from start of administration) | 42 days after starting feeding (day 14 from start of administration) |
| Non-treated group (group fed a regular diet) | 0.8 | 1.0 |
| Saline-administered group | 5.3 | 4.5 |
| 1% clarithromycin aqueous solution-administered group | 5.5 | 1.8 |

(Discussion)
At 28 days from starting the diet (day 0 from starting the administration), there was almost no difference in the number of obstructed meibomian gland orifices between the saline-administered group (fed by HR-AD diet) and the 1% (w/v) clarithromycin aqueous solution-administered group (fed by HR-AD diet), but 42 days after starting the diet (14 days from starting administration), the number of obstructed meibomian gland orifices was remarkably decreased, and meibomian gland concretion was improved in the 1% (w/v) clarithromycin aqueous solution-administered group.

INDUSTRIAL APPLICABILITY

In the present invention, by using clarithromycin as an effective component, it is possible to treat or prevent MGD or meibomian gland concretion.

The invention claimed is:

1. A method for therapy of meibomian gland dysfunction with obstructions of meibomian gland orifices, the method comprising administering an effective amount of clarithromycin to a subject in need thereof.

2. The method according to claim 1, wherein an effective amount of clarithromycin is administered in a dosage form of an ophthalmic solution or ophthalmic ointment.

3. The method according to claim 1, wherein clarithromycin is administered in a dosage form of an ophthalmic solution in an amount of from 0.0001 to 5% (w/v).

4. The method according to claim 1, wherein clarithromycin is administered in a dosage form of an ophthalmic solution in an amount of from 0.01 to 3 (w/v).

5. A method for improving meibomian gland obstruction, wherein the meibomian gland obstruction is caused by reduced secretion type meibomian gland dysfunction, the method comprising administering an effective amount of clarithromycin to a subject in need thereof.

6. The method according to claim 5, wherein an effective amount of clarithromycin is administered in a dosage form of an ophthalmic solution or ophthalmic ointment.

7. The method according to claim 5, wherein clarithromycin is administered in a dosage form of an ophthalmic solution in an amount of from 0.0001 to 5% (w/v).

8. The method according to claim 5, wherein clarithromycin is administered in a dosage form of an ophthalmic solution in an amount of from 0.01 to 3 (w/v).

* * * * *